United States Patent
Bright (10) Patent No.: US 8,377,717 B2
(45) Date of Patent: Feb. 19, 2013

(54) SITE SELECTIVELY TAGGED AND TEMPLATED MOLECULARLY IMPRINTED POLYMERS FOR SENSOR APPLICATIONS

(75) Inventor: Frank V. Bright, Williamsville, NY (US)

(73) Assignee: The Research Foundation of State University of New York, Amherst, NY (US)

( * ) Notice: Subject to any disclaimer, the term of this patent is extended or adjusted under 35 U.S.C. 154(b) by 229 days.

(21) Appl. No.: 12/728,783

(22) Filed: Mar. 22, 2010

(65) Prior Publication Data
US 2010/0233828 A1   Sep. 16, 2010

Related U.S. Application Data

(63) Continuation of application No. 11/006,857, filed on Dec. 8, 2004.

(60) Provisional application No. 60/527,661, filed on Dec. 8, 2003.

(51) Int. Cl.
| | |
|---|---|
| *G01N 21/00* | (2006.01) |
| *G01N 21/77* | (2006.01) |
| *G01N 33/48* | (2006.01) |
| *C08G 63/91* | (2006.01) |
| *C08F 10/00* | (2006.01) |

(52) U.S. Cl. .......... 436/531; 422/68.1; 435/7.1; 436/71; 436/86; 525/50; 525/54.1; 525/333.3; 525/333.7; 525/100

(58) Field of Classification Search .................. None
See application file for complete search history.

(56) References Cited

U.S. PATENT DOCUMENTS

| | | |
|---|---|---|
| 3,966,744 A | 6/1976 | Goldstein et al. |
| 5,162,218 A | 11/1992 | Schultz |
| 5,512,492 A | 4/1996 | Herron et al. |
| 5,714,386 A | 2/1998 | Roederer |
| 6,057,377 A | 5/2000 | Sasaki et al. |
| 6,131,580 A | 10/2000 | Ratner et al. |
| 6,221,604 B1 | 4/2001 | Upadhya et al. |
| 6,287,765 B1 | 9/2001 | Cubicciotti |
| 6,458,599 B1 | 10/2002 | Huang |
| 6,495,352 B1 | 12/2002 | Brinker et al. |
| 6,525,154 B1 | 2/2003 | Shea et al. |
| 6,582,971 B1 | 6/2003 | Singh et al. |
| 6,743,581 B1 | 6/2004 | Vo-Dinh |
| 6,935,165 B2 | 8/2005 | Bashir et al. |
| 7,205,162 B1 | 4/2007 | Mosbach et al. |
| 7,319,038 B2 | 1/2008 | Southard |
| 7,384,589 B2 | 6/2008 | Hart et al. |
| 2002/0144626 A1 | 10/2002 | Schut |

(Continued)

FOREIGN PATENT DOCUMENTS

| | | |
|---|---|---|
| WO | 01/30856 A1 | 5/2001 |
| WO | 02083708 A2 | 10/2002 |

OTHER PUBLICATIONS

Gilardi et al., "Engineering the Maltose Binding Protein for Reagentless Fluorescence Sensing," Anal. Chem., 1994, vol. 66 (21), pp. 3840-3847.*

(Continued)

*Primary Examiner* — Shafiqul Haq
*Assistant Examiner* — Galina Yakovleva
(74) *Attorney, Agent, or Firm* — Hodgson Russ LLP (57) ABSTRACT

This invention provides molecularly imprinted polymers (MIPs) for the detection of analytes, methods for forming the MIPs and detecting the analyte using the MIPs. The MIP comprises templated sites which are formed using a mimic of the analyte such that a reporter compound can be selectively attached at the templated sites, thus providing a site selectively tagged and templated MIP.

13 Claims, 4 Drawing Sheets

U.S. PATENT DOCUMENTS

2004/0106162 A1 6/2004 Glasel et al.
2004/0157804 A1 8/2004 Chen et al.
2006/0019408 A1 1/2006 Waggoner et al.

OTHER PUBLICATIONS

Graham et al., "Development and characterization of molecularly imprinted sol-gel materials for the selective detection of DDT," Anal. Chem, 2002, vol. 74, pp. 458-467.
Kritz et al., "Introducing biomimetic sensors based on molecularly imprinted polymers as recognition elements," Anal. Chem, 1995, vol. 67, pp. 2142-2144.
Pirila-Honkanen, "Thermodynamic and spectroscopic properties of 2-pyrrolidinones. 6. Normalized ET(30) parameters for binary solve mixtures of 2-Pyrrolidinone at 30 and 50C," Journal of Solution Chemistry, 1995, vol. 24, pp. 641-649.
Sreenivasan et al., "Imparting recognition sites in poly (HEMA) for two compounds through molecular imprinting," J. Appl. Polym. Sci., 199, vol. 71, pp. 1823-1826.
Richter-Egger et al., "Spectroscopic investigations of polyamido amine starburst dendrimers with Reichardt's ET-30 dye," Applied Spectroscopy, 2000, vol. 54, pp. 1151-1156.
Rathbone et al., "Molecular Recognition by Fluorescent Imprinted Polymers," Tetrahedron Letters, 2000, vol. 41, pp. 123-126.
Lulka et al., "Molecular Imprinting of Small Molecules With Organic Silanes: Fluorescence Detection," Analytical Letters, 1997 vol. 30, No. 13, pp. 2301-2313.
Makote et al., "Template Recognition in Inorganic—Organic Hybrid Films Prepared by the Sol-Gel Process," Chemistry of Materials, 1998, vol. 10, pp. 2440-2445.
Lulka et al., "Molecular imprinting of Ricin and it's A and B chains to organic silanes: fluorescence detection," Materials Science & Engineering C, 2000, vol. 11, pp. 101-105.
Dong et al., "Recognition of Histamine by a Molecularly Imprinted Polymer Based on Zinc(II)-Protoporphyrin as the Fluorescent Functional Monomer," Analytical Sciences, 2001, vol. 17 (Suppl.), pp. a295-a298.
Leung et al., "A sol-gel derived molecular imprinted luminescent PET sensing material for 2,4-dichlorophenoxyacetic acid," Journal of Materials Chemistry, 2001, vol. 11, pp. 2985-2991.
Zhang et al., "9-(Guanidinomethyl)-10-vinylanthracene: a suitable fluorescent monomer for MIPs," Tetrahedron Letters, 2001, vol. 42, pp. 4413-4416.
Angelides, "Application of Photoactivatable Fluorescent Active-Site Directed Probes to Serine-Containing Enzymes," Biochimica et Biophysica Acta, 1981, vol. 669; pp. 149-156.
Yan et al., "Photochemical functionalization of polymer surfaces and the production of biomolecule-carrying micrometer-scale structures by deep-UV lithography using 4-substituted perfluorophenyl azides," Journal of the American Chemical Society, 1993, vol. 115, No. 2; pp. 814-816.
Bronk et al., "Fabrication of Patterned Sensor Arrays with Aryl Azides on a Polymer-Coated Imaging Optical Fiber Bundle," Analytical Chemistry, 1994, vol. 66, No. 20; pp. 3519-3520.
Albert et al., "Cross-Reactive Chemical Sensor Arrays," Chem. Rev., 100, pp. 2595-2626, 2000 American Chemical Society; published on Web Jun. 24, 2000.
Bailey et al., "Sensing Volatile Chemicals Using Conducting Polymer Arrays," Polymer Sensors and Actuators, pp. 149-181, Osada, Y., DeRossi, D.E., Eds.: Springer-Verlag, Berlin, Germany, 2000.
Stefan et al., "Electrochemical Sensor Arrays," Critical Reviews in Analytical Chemistry, 29(2), pp. 133-153 (1999) CRC Press LLC.
Walt, "Imaging Optical Sensor Arrays," Current Opinion in Chemical Biology 2002, 6, pp. 689-695, 2002 Elsevier Science Ltd., published online Aug. 30, 2002.

Cho et al., "Multianalyte Pin-Printed Biosensor Arrays Based on Protein-Doped Xerogels," Anal. Chem. 2002, vol. 74, No. 24, pp. 6177-6184, 2002 American Chemical Society, published on Web Nov. 12, 2002.
Cho et al., "Integrated Chemical Sensor Array Platform Based on a Light Emitting Diode, Xerogel-Derived Sensor Elements, and High-Speed Pin Printing," Analytical Chimica Acta 470 (2002), pp. 101-110, 2002 Elsevier Science B.V.
Cho et al., "Pin-Printed Chemical Sensor Arrays for Simultaneous Multianalyte Quantification," Anal. Chem. 2002, vol. 74, No. 6, pp. 1462-1466, 2002 American Chemical Society, published on Web Jan. 25, 2002.
Kriz et al., "Molecular Imprinting New Possibilities for Sensor Technology," Analytical Chemistry News & Features, Jun. 1, 1997, pp. 345-349.
Wulff, "Molecular Imprinting in Cross-Linked Materials With the Aid of Molecular Templates—A Way Towards Artificial Antibodies," Angew. Chem. Int. Ed. Engl, 1995, 34, pp. 1812-1832.
Mayes et al., "Molecularly Imprinted Polymers: Useful Materials for Analytical Chemistry?," Trends in Analytical Chemistry, vol. 16, No. 6, 1997, pp. 321-332.
Turkewitsch et al., "Fluorescent Functional Recognition Sites Through Molecular Imprinting. A Polymer-Based Fluorescent Chemosensor for Aqueous Camp," Anal. Chem 1998., vol. 70, No. 10, pp. 2025-2030, 1998 American Chemical Society, published on Web Apr. 17, 1998.
Jenkins et al., "Polymer-Based Lanthanide Luminescent Sensor for Detection of the Hydrolysis Product of the Nerve Agent Soman in Water," Anal. Chem. 1999, vol. 71, No. 2, pp. 373-378, 1999 American Chemical Society, published on Web Dec. 10, 1998.
Matsui et al., "Molecularly Imprinted Polymer as 9-Ethyladenine Receptor Having a Porphyrin-Based Recognition Center," J. Am. Chem. Soc. 2000, 122, pp. 5218-5219, 2000 American Chemical Society, published on Web May 12, 2000.
Liao et al., "Building Fluorescent Sensors by Template Polymerization: The Preparation of a Fluorescent Sensor for L-Tryptophan," Bioorganic Chemistry 27 (1999), pp. 463-476, 1999 Academic Press.
Avnir et al., "Encapsulation of Organic Molecules and Enzymes in Sol-Gel Glasses A Review of Novel Photoactive, Optical, Sensing, and Bioactive Materials," pp. 384-404, 1992 American Chemical Society.
Avnir et al., "Organically Doped Sol-Gel Porous Glasses: Chemical Sensors, Enzymatic Sensors, Electrooptical Materials, Luminescent Materials and Photochromic Materials," Sol-Gel Optics—Processing and Applications, Chapter 23, pp. 539-582, Klein, L.C., Ed., Kluwer: Boston, 1994.
Dave et al, "Sol-Gel Encapsulation Methods for Biosensors," Analytical Chemistry, vol. 66, No. 22, 1994, pp. 1120-1127, 1994 American Chemical Society.
Cushman et al., "Synthesis and Anti-HIV Activities of Low Molecular Weight Aurintricarboxylic Acid Fragments and Related Compounds," J. Med. Chem. 1991, 34, pp. 337-342, 1991 American Chemical Society.
Whitcombe et al., "A New Method for the Introduction of Recognition Site Functionality into Polymers Prepared by Molecular Imprinting: Synthesis and Characterization of Polymeric Receptors for Cholesterol," J. Am. Chem. Soc. 1995, 117, pp. 7105-7111, 1995 American Chemical Society.
Sellergren, "Noncovalent Molecular Imprinting: Antibody-Like Molecular Recognition in Polymeric Network Materials," Trends in Analytical Chemistry 1997, vol. 16, No. 6, pp. 310-320, 1997 Elsevier Science B.V.
Whitcombe et al., "Covalent Imprinting Using Sacrificial Spacers," Tech. Instrumn. Anal. Chem. 2001, 23, 203-12, pp. 203-212.

* cited by examiner

SITE SELECTIVELY TAGGED AND TEMPLATED MOLECULARLY IMPRINTED POLYMERS FOR SENSOR APPLICATIONS

CROSS REFERENCE TO RELATED APPLICATIONS

This application is a continuation of U.S. patent application Ser. No. 11/006,857 filed on Dec. 8, 2004, which in turn claims the priority of U.S. Provisional application No. 60/527,661 filed on Dec. 8, 2003, the disclosures of which are incorporated herein by reference.

STATEMENT REGARDING FEDERALLY SPONSORED RESEARCH OR DEVELOPMENT

This work was funded by Grant No. CHE-0078101 and CHE-0315129 from the National Science Foundation. The Government has certain rights in the invention.

FIELD OF THE INVENTION

This invention relates to field of detection of analytes by the use of selectively tagged and templated molecularly imprinted polymers (SSTT-MIPs).

BACKGROUND OF THE INVENTION

Americans spend billions of dollars annually on the detection and quantification of chemical substances. Most of these measurements are performed in well-outfitted laboratories, requiring skilled personnel, large amounts of costly reagents, and long analysis times. Also, the demands for use in clinical point-of-care testing or for field deployment necessitate small, integrated analytical platforms. Many of these needs have helped to spark chemical sensor development [1]. Similarly, the ever growing need to simultaneously measure "everything" in a sample [2] has pushed the development of artificial "noses" and "tongues" [3] which depend upon chemical and biochemical sensor array strategies [4-10]

Presently, there is a need to develop new devices which overcome the disadvantages of presently used methods. Detection methods which allow the simultaneous quantification of multiple analytes in a sample, are less expensive and more simple to construct and operate, are accurate, precise and reliable, and provide adequate detection limits and selectivity would be a welcome advance in the field of analyte detection.

On general method which has been tried is the use of "biosensors." In the generic biosensor, an immobilized biorecognition element (e.g., an antibody, aptamer, DNA oligonucleotide, enzyme, lectin, signaling protein, transport protein) serves to selectively recognize a target analyte and the binding or conversion (if the analyte is a substrate) event leads to an optical, mass, thermal, or electrochemical response that is related to the analyte concentration within the sample.

Although biosensor development may appear simple, there are many fundamental issues associated with developing analytically useful biosensors. For example, traditional strategies depend upon identifying an appropriate biorecognition element that can selectively recognize the target analyte. A suitable detection/transduction method is used and the biorecognition element is immobilized [11-13] such that it retains its native activity/affinity and selectivity. The biorecognition element—the biosensor's heart in a traditional design—needs to remain stable over time, the target analyte needs to have access to the biorecognition element, and the analyte-biorecognition element association/interaction needs to be reversible or at least easily dissociated/reset following each measurement. The foregoing shortcomings have limited the application of biosensors in analyte detection.

Over the past decade, the introduction of specific binding domains within synthetic polymers by template-directed cross-linking of functional monomers has attracted considerable attention [15]. Molecular imprinting involves arranging polymerizable functional monomers around a template (pseudo-target analyte or the actual target analyte) followed by polymerization and template removal. Arrangement is typically achieved by: (i) non-covalent interactions (e.g., H-bonds, ion pair interactions) or (ii) reversible covalent interactions. After template removal, these molecularly imprinted polymers (MIP) can recognize and bind specific chemical species (i.e., the template or template analogs).

Potential advantages of MIP-based materials include: specificity comparable to a biorecognition element; robustness and stability under extreme chemical and physical conditions; and an ability to design recognition sites for analytes that lack suitable biorecognition elements. MIPs have been developed for (not an exhaustive list) proteins, amino acid derivatives, sugars and their derivatives, vitamins, nucleotide bases, pesticides, pharmaceuticals, and polycyclic aromatic hydrocarbons. However, according to Lam [16], one of the major issues in the development of MIP based biomimetic sensors is signal transduction.

There are several reports of MIP based sensors that exploit luminescence as the transduction modality. For example, the Powell group [17a] formed cAMP-imprinted organic polymers by using trans-4-[p-(N,N-dimethylamino)stryl]-N-vinylbenzylpyrimidinium chloride (fluorophore), trimethylolpropane trimethacrylate, 2-hydroxyethyl methacrylate, and the initiator, 2,2'-azobisisobutyronitrile (AIBN). These MIPs showed a 20% change in fluorescence in the presence of 1 millimolar cAMP and they were selective for cAMP over cGMP. The Murray group [17b] prepared Soman-imprinted organic polymers by using $Eu(R)_3(NO_3)_3$ (R=pinacolyl methylphosphonate or divinylmethyl benzoate) (fluorophore), styrene, and AIBN. These MIPs were able to detect Soman down to 750 parts per quadrillion and interferences from organophosphorous pesticides was minimal. The sensor response time was 8 min. The Takeuchi group [17c] reported a fluorescence-based MIP sensor for the detection of 9-ethyladenine (9-EA). This sensor was based on templating 9-EA with 5,10,15-tris(4-isopropylphenyl)-20-(4-metharcyloyloxyphenyl)porphryin zinc (II) (fluorophore) and methacrylic acid. In $CH_2Cl_2$, these polymers exhibited a 9-EA binding affinity of $7.5 \times 10^5$ $M^{-1}$, were selective over adenine, 4-aminopyridine, and 2-aminopyridine, and yielded a fluorescence change of 40% in the presence of 250 micromolar 9-EA. The Wang group [17d] reported on a fluorescence-based MIP sensor for detecting L-tryptophan that used a dansylated dimethylacrylic acid monomer (fluorophore), ethyleneglycol dimethylacrylate, and AIBN. In operation the authors loaded a mobile quencher, 4-nitrobenzaldehyde (4-NB), into the MIP which quenched the dansyl emission. Upon addition of L-tryptophan some of the 4-NB was liberated/blocked from accessing the dansyl residue and the dansyl fluorescence increased. The change in fluorescence upon adding 10 millimolar L-tryptophan was 45%. The presence of an equivalent amount of D-tryptophan, L-phenylalanine, and L-alanine caused 32%, 27%, and <9% changes in fluorescence. The Lam group [16] used a photoinduced electron transfer (PET) strategy to form a fluorescence-based MIP for the detection of 2,4-dichlorophenoxyacetic acid (2,4-D) within a templated sol-gel-derived xerogel. In this work, the authors copolymerized 3-[N,N-bis(9-anthrylmethyl)amino)] propyltriethoxysilane (fluorophore) with tetraethoxysilane (TEOS) and phenyltrimethoxysilane (PtrMES) using 2,4-D as the template. The so formed MIP exhibited a change in fluorescence with pH (apparent pKa near 7.2) and it yielded a 15% decrease in fluorescence in the presence of 750 micromolar 2,4-D. Tests with benzoic acid and acetic acid at similar concentrations did not cause significant interference.

Most recently, Edmiston and coworkers [17e] reported an approach to fabricate a fluorescence-based xerogel MIP for the detection of the pesticide 1,1-bis(4-chlorophenyl)2,2,2-trichloroethane (DDT) by using a sacrificial spacer (SS) scheme [18] wherein they reacted 3-isocyanatopropyltriethyoxysilane with 4,4'-ethylidenebisphenol to form the SS. They then prepared the fluorescent monomer by reacting 3-aminoproplytriethoxysilane (APTES) with the fluorophore 4-chloro-7-nitrobenzofurazan (NBD) (attaching the NBD to the APTES amine, NBD-APTES). The imprinted xerogel was then formed by mixing NBD-APTES, SS, and bis(trimethoxysilyl)benzene followed by a typical acid hydrolysis protocol. Once the xerogel was formed, the authors cleaved the SS carbamate bond with dilute $LiAlH_4$ to form amine residues within the template site, and liberating the SS from the xerogel. The sensor responded to DDT (3% change in NBD fluorescence) and the templated xerogels offered selectivity for DDT over potential interferents (e.g., anthracene (A), 2,2-bis(4-chlorophenyl)-1,1-dichloroethylene (p,p-DDE), 1-(2-chlorophenyl)-1-(4-chlorophenyl)-2,2-dichloroethane(o,p-DDD), 2,2-bis(4-chlorophenyl)-1,1-dichloroethane (p,p-DDD), diphenylmethane (DPM), 4,4'-dibromobiphenyl (DBBP), 4,4'-bis(chloromethyl)-1,1'-biphenyl (BCP)). The DDT detection limits were at the single digit part per billion level.

However, in all previous work on luminescence based MIP sensors, no strategy has been developed to ensure that the luminescent reporter molecule is actually in immediate proximity to the analyte when the analyte binding occurs.

SUMMARY OF THE INVENTION

The present invention presents a method for forming a reliable chemical sensor platform based on site selectively tagged and templated molecularly imprinted polymers. The SSTT-MIP strategy used in the present method provides a way to form a MIP having a templated site specific for an analyte and at which a reporter molecule can also be attached. In this way, analyte detection can be carried out with a higher efficiency in comparison to methodologies without any provision for such positioning. With this invention, measurement characteristics such as signal-to-background and signal-to-noise ratios are expected to be improved over those of similar MIP methods such as those described by Edmiston.

The method comprises the following steps. A mimic of the analyte, termed herein as the sacrificial spacer molecule template (SSMT), is identified or created. Next, the SSMT is incorporated into a polymer platform by initiating polymerization of the unpolymerized components in the presence of the SSMT resulting in the formation of polymer platforms having templated sites at which the SSMT is bonded by a plurality of reactive groups. The SSMT is then removed from the polymer platform, creating within the platform one or more templated sites for the target analyte and one or more reporter molecules. The SSMT is chosen such that removal of the SSMT leaves reactive groups for the binding of the analyte and at least one reporter molecule at the template site. Following removal of the SSMT, the template site is contacted with the analyte which bonds to it thereby blocking all reactive groups except for the group to which reporter binding (i.e., tagging) is to take place. This complex is then exposed to the reporter molecule. The analyte is removed, and the resulting polymer platform is a site-selectively tagged and templated molecularly imprinted polymer (SSTT-MIP).

The present invention also provides molecularly imprinted polymer platforms in which templated sites are formed for specific analytes. In one embodiment, the polymer platforms can be provided wherein the templated sites have at least one reporter molecule bonded to a reactive group at the site. In one embodiment, the polymer platform comprises xerogels or aerogels.

This method can be used to develop sensors for the detection of a wide variety of analytes including those for which no known biological recognition molecules have been reported.

DETAILED DESCRIPTION OF THE INVENTION

The present invention provides site selectively tagged and templated molecularly imprinted polymers (SSTT-MIP). The SSTT-MIPs have a reporter molecule strategically placed to enhance the efficiency of detection of the analyte. While not intending to be bound by theory, it is thought that changes in the physicochemical properties (e.g., dielectric constant, refractive index, dynamics, etc.) of the immediate microenvironment that surrounds the reporter molecules (referred to herein as a reporter's cybotactic region) cause changes in the reporter molecule's absorbance, excitation and emission spectra, excited-state luminescence lifetime and/or luminescence polarization. As a result, a greater change in reporter absorbance/luminescence properties (i.e., analytical signal) is expected to be realized when a reporter molecule and the MIP template site share some or all of the reporter molecule's cybotactic region. Hence, when analyte molecules are bound to a MIP template site thereby changing the physicochemical properties of the MIP template site, the binding is sensed simultaneously by the reporter molecule at the MIP template site.

In one embodiment of the invention, reporter molecules are exclusively present at the template sites, thereby reducing the signal to noise ratio and signal to background ratio. In this embodiment, very few or no reporter molecules are present in the polymer matrix (i.e., other than at the templated sites).

The present invention also provides a method for fabricating a MIP in which a reporter molecule can be selectively installed at a templated site such that during the detection of the analyte, the reporter molecule is positioned in close proximity to the analyte (i.e, within the reporter molecules cybotactic region).

As used herein, the term "molecularly imprinted polymer" or "MIP" refers generally to a gel or polymeric mold-like structure having multiple molecular-scale templated sites, each of which has the ability to specifically bind an analyte molecule. The templated sites complement the shape of at least a portion of an analyte molecule. Furthermore, the templated sites contain interactive moieties that have a positioning which matches the spatial arrangement of moieties on the analyte. The moieties in the templated site are complementary to the moieties on the analyte. By complementary, it is meant that moiety in the templated site can interact with the positionally corresponding moiety on the analyte to form a bond or other attractive association, such as, for example, an electrostatic, covalent, ionic, hydrophobic, hydrogen-bonding, or other interaction.

As will be recognized by those of skill in the art, MIPs are typically formed by mixing analyte molecules with one or more functional monomers to form imprint/monomer complexes (wherein the imprint molecule interacts or bonds with a complementary moiety of the functional monomer via covalent, ionic, hydrophobic, hydrogen-bonding, or other interactions). The monomer/analyte complexes are then polymerized into a crosslinked polymer matrix. The analyte molecules are subsequently dissociated/cleaved from the functional monomers and thereby removed from the polymer matrix to leave templated recognition sites. The templated sites have a shape which is specific to the analyte. The molecular-scale cavities contain moieties which are complementary to the analyte molecule, giving the cavity the ability to selectively bind the analyte.

In contrast to MIP methods of the prior art, in the method of the present invention, a mimic of the analyte, termed herein as the sacrificial spacer molecule template (SSMT) is identified or created, and then incorporated within a polymer platform. The SSMT preferably bears close structural resemblance to the target analyte. Furthermore, the SSMT is chosen such that it forms bonds with the polymer platform in excess of the number of those which will be formed by the bound analyte. The SSMT should have at least one additional reactive group so as to be able to bind to the polymer matrix at an additional site relative to an intended analyte. In one embodiment, the number of reactive groups on the SSMT which link it to the polymer platform, is at least one more than the number of reactive groups on the corresponding analyte. In a further embodiment, the SSMT is structurally identical to the analyte except for the number and identity of the reactive groups which link to the polymer platform. The groups which participate in the SSMT-polymer linkages may be included in the SSMT. These SSMT polymer linkages are ultimately cleaved in the removal of the SSMT.

In general, analytes and the corresponding SSMT are structurally similar, often differing by the presence of an additional functional group on the SSMT. However, chemically different molecules may be similarly shaped, and thus, close structural similarity may not be a complete characterization of the relationship between analyte and SSMT. Furthermore, there are many slight structural modifications which may give rise to acceptable SSMTs for a given analyte. Other effects, such as intermolecular hydrogen bonding, ionic interactions, aggregation, encapsulation, dimerization, may still result in an SSTT-MIP which exhibits a binding preference toward the analyte molecule.

The removal of the SSMT results in templated sites which are referred to herein for the sake of simplicity as cavities, within the polymer platform. Exposed at each templated site are reactive groups which are responsible for target analyte recognition. However, as a consequence of the additional reactive group(s) mentioned above, when the SSMT is cleaved from the cavity, the cavity bears one or more reactive groups in excess of the groups needed to bind an analyte molecule. The extra group(s) is (are) used to bond with reporter molecules. Once the reporter molecule(s) is (are) bound at the templated site, the absorbance/luminescence from the SSTT-MIP is measured and a change in UV, visible or IR absorbance/luminescence properties of the reporter (e.g., absorbance spectra, excitation and emission spectra, excited-state luminescence lifetime and/or luminescence polarization) indicates the presence of an analyte molecule at the templated site. The total change in absorbance/luminescence is generally proportional to the concentration of analyte molecule in the sample. Thus, analyte-dependent calibration curves can readily be constructed.

Figure 1:
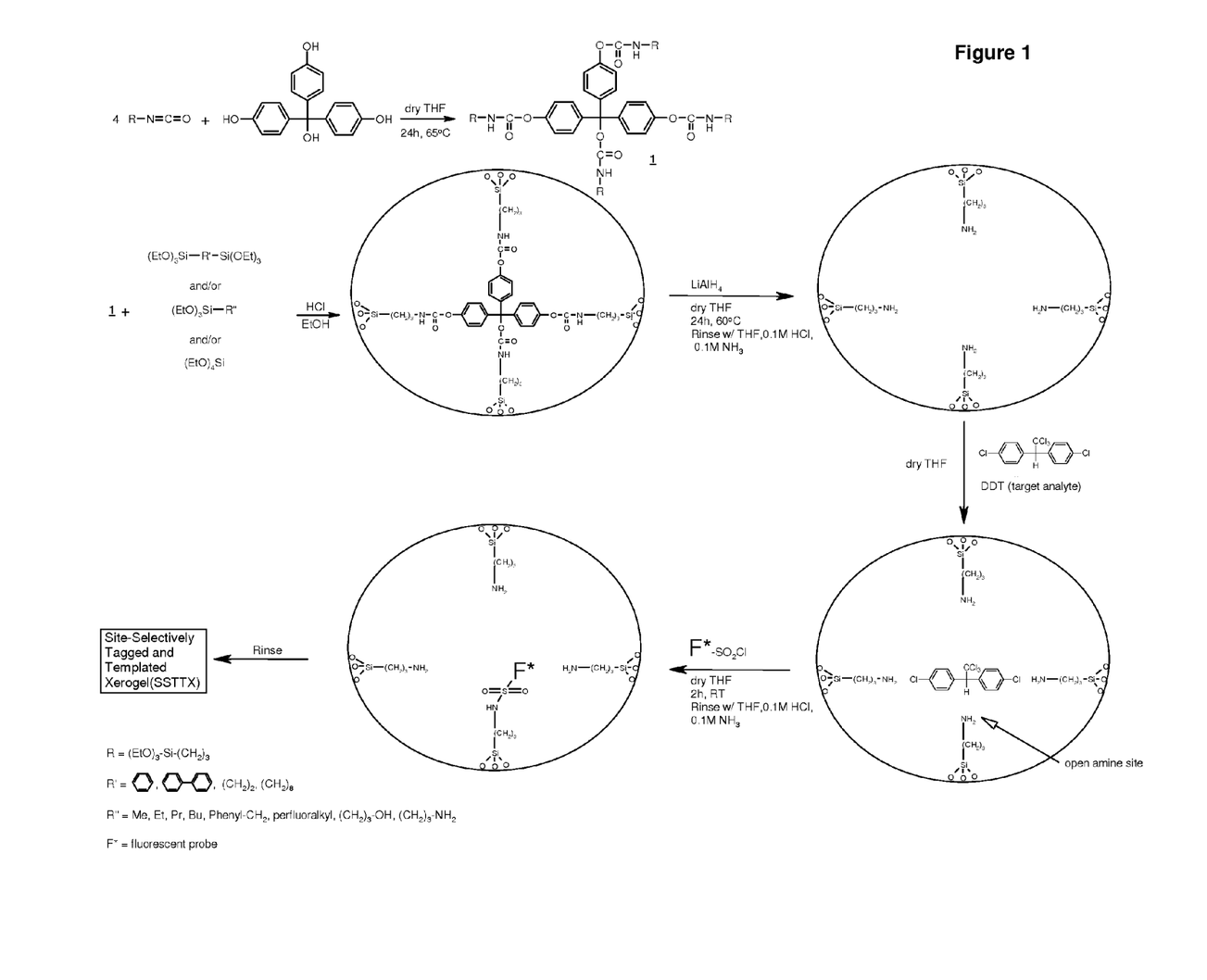
FIG. 1 is a representation of a typical reaction scheme to produce a site-selectively tagged and templated molecularly imprinted polymer (SSTT-MIP) based on a sol-gel-derived xerogel platform. The target analyte is DDT.

In one embodiment, the SSMT, in comparison to its target analyte, possesses one additional functional residue, as illustrated further in FIG. 1 in the case of the analyte DDT and an appropriate SSMT molecule, Compound 1. Compound 1 is an analog of DDT with four $(EtO)_3$—Si-tipped carbamate-containing groups. DDT, in contrast, has three Cl-containing functional groups in positions which are analogous to three of the positions of the above-mentioned groups on Compound 1. A MIP is created by conducting a polymerization with one or more functional monomers which binds to the Compound 1 through the available alkoxide functional groups. The polymerization occurs around the SSMT, giving a polymer platform which is linked to the SSMT via the $(EtO)_3$—Si carbamate groups. The SSMT is then cleaved from the polymerized platform to give a MIP with templated sites, each site having four amino groups extending into it. The MIP is then exposed to DDT, which binds into the template site with an affinity which depends, in part, on the composition of the polymer and its preparation protocol. -The DDT molecules bind to the template site by also interacting with three of the four amino groups in the template site (i.e., each of the three Cl residues on DDT hydrogen bonds to an —$NH_2$ residue within the template site). Because of the "extra" —OH residue on Compound 1, when it is cleaved from the templated cavity using the foregoing step, an amine residue in addition to those needed to bind the analyte, DDT, is formed at the template site. Thus, within the template site there is a single free amine residue that is not bound to the analyte, DDT. The free amine residue is also not blocked by the presence of the analyte, DDT. This free amine residue within the template site is then site-selectively tagged with a reporter molecule, for example, Lissamine™ or rhodamine B sulfonyl chloride, to place a reporter molecule such that its cybotactic region largely overlaps the templated site where analyte will bind. The analyte and any unreacted luminescent probe are then washed from the polymerized platform to produce the SSTT-MIP. The use of a hydroxyl residue and carbamate chemistry is an illustrative example; and one skilled in the art will recognize other strategies. Preferred are chemistries which can be used without appreciably affecting the integrity of the polymer platform, with the use of carbamate linkages being most preferred.

It should be noted that after dissociation from the SSTT-MIP, the SSMT may be modified. For instance, in the example of FIG. 1, the nitrogen atom from each carbamate linkage is left behind as an amine residue when the linkage is cleaved. The modified SSMT molecule is termed herein as SSMT' (SSMT prime).

The present invention can be used with chemistries in which the bonds between the functional monomers and SSMT, created before polymerization, are dissociated/cleaved upon release of the SSMT. Such a situation could arise for example, in the case of a hydroxyl-containing functional monomer which forms an ester linkage with a carboxylic acid-containing-SSMT, which is cleaved upon release of the SSMT from the SSTT-MIP formed from polymerized functional monomer. However, it is preferred to import the entire linkage to be cleaved (carbamate as in the above example) with the SSMT (as done in FIG. 1). In such cases, the SSMT is characterized as missing a portion of the linkage which remains attached to the cavity in order to bind with the analyte.

Many different types of polymer systems can be used in the method of the present invention. As an illustrative example, a sol-gel derived xerogel can be used. However, the approach can easily be adapted to other MIPs based on aerogels or natural or synthetic polymer systems. However, sol-gel-derived xerogels and aerogels are convenient because the xerogels are nanoporous materials with physicochemical properties and pore sizes that can be tuned by ones choice of precursor(s) and the processing protocol such as described in references 19-28.

In general, the polymer used in the method of this invention should be such that the chosen SSMT can bind to or otherwise interact chemically to at least some of its component momomers prior to polymerization. Thus, for example, an SSMT which has linkage groups which containing terminal $(EtO)_3$—Si— groups, such as the $(EtO)_3$—Si-carbamate groups shown in FIG. 1, can be used with a polymerization system which contains polymerization precursors which can form the siloxane by hydrolyzing with this alkoxide-based SSMT. Non-limiting examples of acceptable polymerization precursors are, as shown in the figure, $(EtO)_3$—Si—R'—Si-$(EtO)_3$ and $(EtO)_3$—Si—R" groups. Other examples are known to those skilled in the art (cf., references 19-28).

For sacrificial spacer molecule templates (SSMTs) that contain multiple reactive sites, these additional sites can be blocked (protected) by using protecting groups. Examples of such protecting groups are benzyloxycarbonyl, t-butoxycarbonyl (t-BOC), 9-fluorenylmethoxycarbonyl (Fmoc), or phenyl-$SO_2Cl$). Such protection/deprotection is known to those skilled in the art and is described in reference 29.

In general, the SSTT MIP method is particularly suited for analytes for which a suitable SSMT analog having one or more extra functional groups with respect to the analyte can be prepared.

The SSTT-MIP should be able to associate or bind with the analyte. For instance, the association shown in FIG. 1 is an example of (hydrogen bonding as well as hydrophobic and— interactions). Other types of associations are hydrophobic, hydrogen-bonding, etc. and combination of interactions that exploit specific chemical aspects of the analyte and the polymer-based platform.

The reporter molecule in the present invention may be a luminophore or a chromophore. A binding group can be attached to the reporter molecule or in some cases, the reporter molecule may already have a binding group attached. In the preparation of the SSTT-MIPs, the reporter molecules can be directly bonded to the template site via the binding group or indirectly by using a connecting moiety between the binding group and the luminophore/chromophore. In one embodiment, the reporter is a luminophore connected to a binding group via a connecting group. Binding groups are commercially available (such as from Molecular Probes). A non-limiting example of a reporter comprised of a luminophore, a connecting moiety, and a —$SO_2Cl$ binding group is illustrated specifically in FIGS. 1 and 2.

The luminophore could be an organic or inorganic species. Examples of luminophores include organic species like fluorescein, BODIPY, rhodamine, organometallic complexes like tris(4,7-diphenyl-1,10-phenanthroline)ruthenium(II) ([Ru$(dpp)_3]^{2+}$ and luminescent nanoparticles (i.e., quantum dots). The quantum dots may have elemental silicone (Si), cadmium sulfide (CdS) and zinc selenite (ZnSe)

The connecting moiety (also referred to herein as a tether) can be one of any possible natural or synthetic groups that have been used to space residues apart from one another in the chemical sciences. General examples of connecting moieties are methylene chains, ether chains, polydimethylsiloxane chains, polystyrene chains, amino acid chains, and any other organic/inorganic oligomer.

Specific examples of binding groups which can be used to form linkages with specific types of groups attached to the templated site are as follows: to tag/label amine residues one can use isothiocyanates, succinimidyl esters, carboxylic esters, tetrafluorophenyl esters, carbonyl azides, sulfonyl chlorides, arylating agents and aldehydes; to tag/label thiol residues one can use iodoacetamides, maleimides, alkyl halides, arylating agents, and disulfides; to tag/label alcohol residues one can use dichlorotriazines, N-methylisatoic anhydride, aminophenylboronic acids, isocyanates prepared from acyl azides, and acyl nitriles; and to tag/label carboxylic acids one can use hydrazines, hydroxylamines amines, carbodiimides, esterification reagents, diazoalkanes, alkyl halides, and trifluoromethanesulfonates.

It is preferred that the connecting moiety not be so long as to remove the chromophore/luminophore from the template site to such a degree that the effect on the chromophore/luminophore of the analyte molecule binding to the template site is too small to detect. Accordingly, some overlap between the reporter molecule's cybotactic region and the template site is desirable. Alternatively, the reporter molecule can be directly attached to one of the aforementioned binding groups.

The reporter molecule generally has a luminescence spectrum in the UV, visible and/or IR; however, non-luminescent dye molecules that are responsive to their physicochemical environments can also be used as reporter molecules (e.g., 4-nitroaniline, and 2,6-diphenyl-4-(2,4,6-triphenyl-1-pyridinio)phenolate (Reichardt's dye 30), 2,6-dichloro-4-(2,4,6-triphenyl-1-pyridinio)phenolate (Reichardt's dye 33), and N,N-diethyl-4-nitroaniline) in the SSTT-MIP strategy. The chromophore's/luminophore's absorbance and/or emission depends on the physicochemical properties of its local environment such that the molar absorbance, absorbance spectrum, emission quantum yield, emission spectrum, excited-state lifetime, and/or luminescence polarization are (one or all) modulated to some degree by the local physicochemical properties that surround the reporter molecule. This change in physicochemical properties is modulated by the binding of the analyte molecule to the template site and is detected as a change in the reporter molecule's molar absorbance, absorbance spectrum, emission quantum yield, emission spectrum, excited-state lifetime, and/or luminescence polarization. Examples of suitable luminophores include dansyl, fluorescein, rhodamine, NBD, and tris(4,7-diphenyl-1,10-phenanthroline)ruthenium(II) ([Ru$(dpp)_3]^{2+}$. Examples of suitable chromophores include 2,6-diphenyl-4-(2,4,6-triphenyl-1-pyridinio)phenolate (Reichardt's dye 30), 2,6-dichloro-4-(2,4,6-triphenyl-1-pyridinio)phenolate (Reichardt's dye 33), and N,N-diethyl-4-nitroaniline.

Below are examples of analytes that can be detected by the present SSTT-MIP methods outlined in FIGS. 1 and 2. The possible analyte molecules include, but are not limited to, pharmaceuticals, steroids, prostaglandins, glycosides, deoxyribonucleosides, deoxyribonucleotides and the like. A non-limiting list of analytes that can be detected by this method and their sacrificial spacer molecule template are shown in Table 1.

TABLE 1

Examples of sensor target analytes (left column) and SSMT (right column).

| Pharmaceutical | |
|---|---|
| Pheytoin | 5-(p-Hydroxyphenyl)-5-phenylhydantoin |
| Codeine | Morphine |
| Heroin | 3-Acetylmorphine |
| Cocaine | p-Hydroxycocaine |
| Δ9-THC | 8-α-Hydroxy-Δ9-THC |
| Tetracycline | Oxytetracycline |
| Morphine | Nalbuphine |
| Steroids | |
| Testosterone | 4-Hydroxytestosterone |
| Estradiol | 4-Hydroxyestradiol |
| Progesterone | 17-α-Hydroxyprogesterone |
| Cholesterol | 22(r)-Hydroxycholesterol |
| Prostaglandins | |
| Prostaglandin A2 | 19(R)-Hydroxyprostaglandin A2 |
| Prostaglandin B2 | 19(R)-Hydroxyprostaglandin B2 |
| Prostaglandin E1 | 19(R)-Hydroxyprostaglandin E1 |
| Prostaglandin E2 | 19(R)-Hydroxyprostaglandin E2 |
| Prostaglandin F1a | 19(R)-Hydroxyprostaglandin F1a |
| Prostaglandin F2a | 19(R)-Hydroxyprostaglandin F2a |
| Prostaglandin F2a | 19(R)-Hydroxyprostaglandin F2a |
| Glycosides | |
| Methyl α-D-glucopyrnoside | α-D-glucopyranose |
| Methyl β-D-glucopyrnoside | β-D-glucopyranose |
| Digitoxin | Digoxin |
| 2-Deoxyribose | Ribose |

The SSTT-MIP strategy is particularly effective in the preparation of sensors to detect and quantify pharmaceuticals (e.g., phenyloin, codeine, heroin), prostaglandins (e.g., A2, B2, F1a), steroids (testosterone, estradiol, progesterone), and glycosides (methyl-D-glucopyranoside, digitoxin, 2-deoxyribose). However, the method can be used to prepare sensors for the detection of a wide range of analytes.

Figure 2:
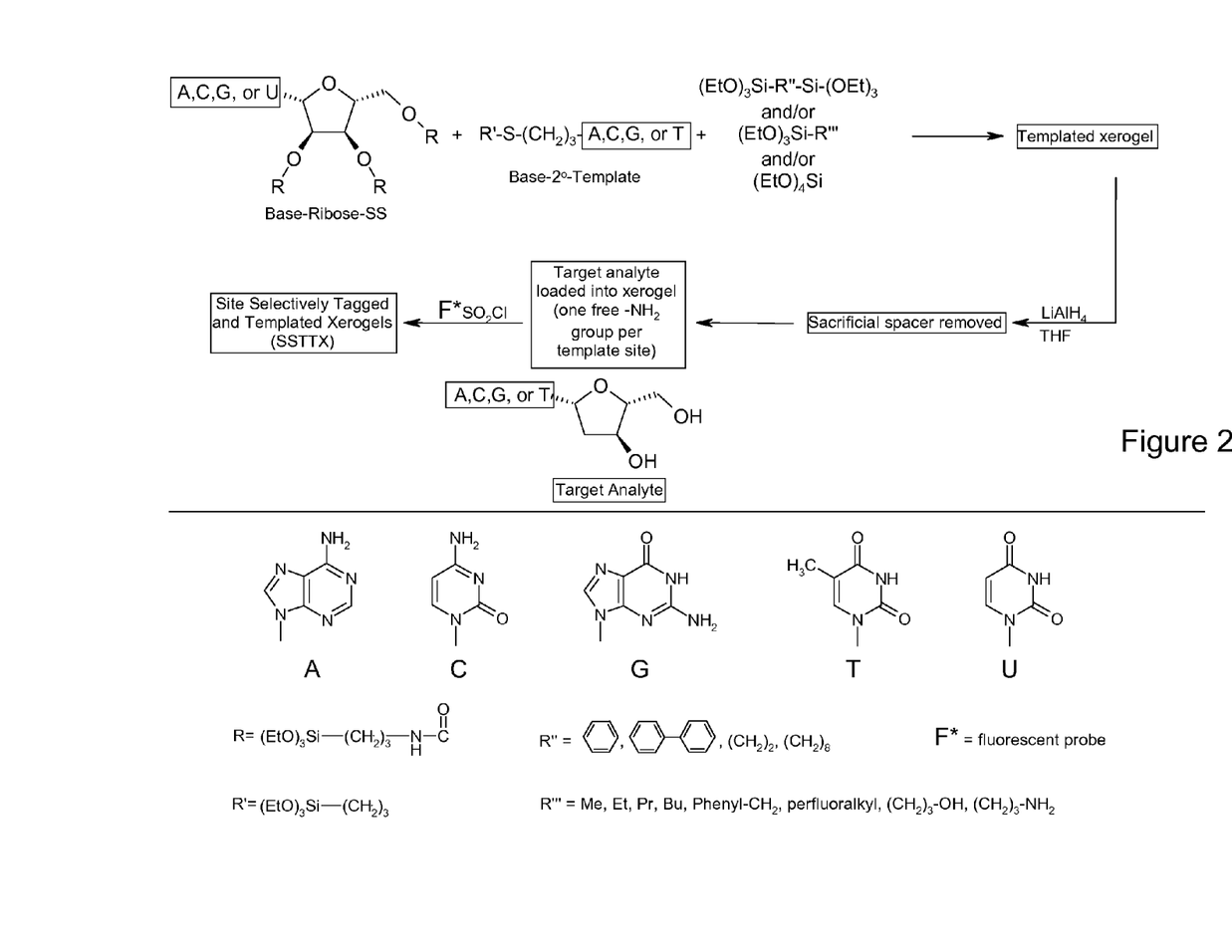
FIG. 2 is a representation of a binary templating strategy for forming a deoxynucleoside selective SSTT-MIP sensor element.

For the detection of deoxyribonucleotides, a binary templating strategy can be used as shown in FIG. 2 to form the SSTT-MIPs. The base ribose sacrificial spacer (Base-Ribose-SSMT) is formed by using the carbamate formation chemistry illustrated in FIG. 1. The base residue on the Base-ribose-SSMT can be selected to match the base on the target analyte except that uracil (U) is used to template thymine (T). The amine sites on the bases can be protected as needed using the Fmoc protection/deprotection to prevent urea formation. The Base-Ribose-SSMT can be mixed (1:1) with the appropriate secondary base template (Base-2°-SSMT) and the main component of the xerogel (i.e., $(EtO)_3Si$—R"—$Si(EtO)_3$, $Si(EtO)_3$, and/or $(EtO)_4Si$)), the templated xerogel formed, the sacrificial spacer removed, and the template site is site-selectively tagged with a chromophore/luminophore. The base residue on the Base-2°-SSMT can be selected to complement the base on the target analyte (such as A for T and G for C and vice versa). The Base-2°-SSMT can be prepared in two steps. As an example, Leonard's method [30] can be used to produce 9-(3-chloropropyl)adenine, 9-(3-chloropropyl)guanine, 3-(3-chloropropyl)thymine, and 3-(3-chloropropyl)cytosine. The derivitized bases are then reacted with 3-mercaptopropyl-triethyoxysilane (MPTES) to form Base-2°-SSMT shown in FIG. 2.

Figure 3:
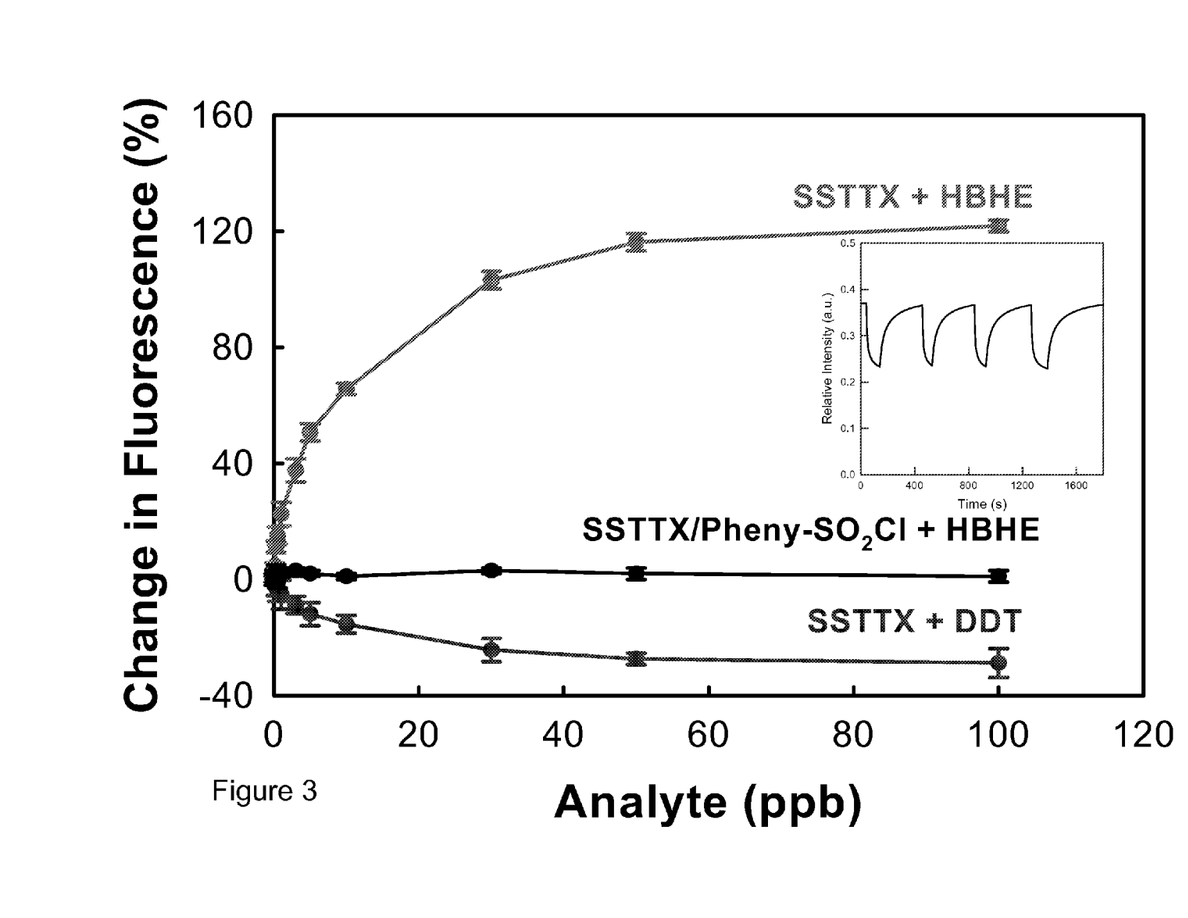
FIG. 3 is a representation of a response profile for a SSTT-MIP sensor that was designed (see FIG. 1) for the detection of DDT. HBHE is 1-hydroxy-2,2-bis(4-hydroxyphenyl)ethane; a hydroxylated analog of DDT.
Figure 4:
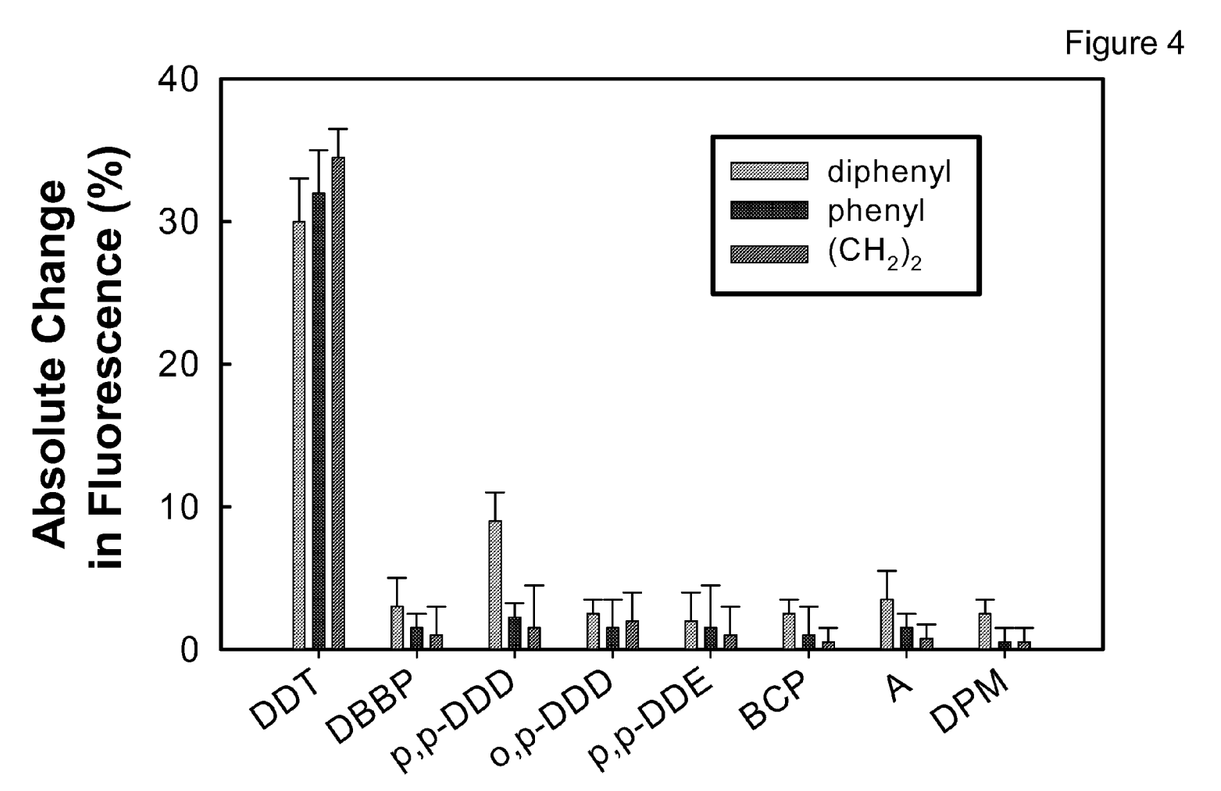
FIG. 4 is a representation of the response from three different SSTT-MIP sensors, each templated for DDT, when challenged with 100 ppb of the indicated molecules. The three SSTT-MIP sensors were derived from different precursors having different R' residues (a non-exhaustive listing of example R' residues are defined in the inset and FIG. 1).

In one embodiment of the invention, multiple tunable sensors can be designed and developed for each target analyte. Here, simultaneous screening of SSTT-MIP libraries can be performed to optimize SSTT-MIP analytical performance and identify sets of SSTT-MIPs wherein the response characteristics, within the set, exhibit the greatest diversity for a given analyte. In one illustration of this (FIG. 3) response data are presented to demonstrate that SSTT-MIPs can yield substantial differences in response for one analyte over another. A second example is presented in FIG. 4 showing the significant changes in response from an SSTT-MIP platform are possible simply by changing one of the precursors that is used to form the xerogel from $(EtO)_3$—Si—$(CH_2)$-$_2$—Si—$(OEt)_3$ to $(EtO)_3$—Si-phenyl-Si—$(OEt)_3$ to $(EtO)_3$—Si-biphenyl-Si—$(OEt)_3$ to create three different xerogel-based SSTT-MIPs.

By using such multiple sensors in concert, the overall detection accuracy, precision, and dynamic range can be improved. False positives and negatives may also be more readily detected by using multiple tunable sensors and redundant detection schema.

Arrays of discrete SSTT-MIP-based sensor elements can be formed on the face of a light source and detected with an array-based detector. Formation of sensor arrays on the face of a light emitting diode (LED) and the simultaneous detection of multiple analytes are described in U.S. Pat. Nos. 6,492,182, 6,582,966 and 6,589,438 incorporated herein by reference. Each SSTT-MIP-based sensor element can serve as an individual sensor for a particular target analyte. In operation, the LED serves as the light source to simultaneously excite the chromophores/luminophores within all the SSTT-MIP sensor elements on the LED face and the target analyte-dependent absorbance/emission from all the SSTT-MIP-based sensor element can be detected by an array detector (e.g., charge coupled device (CCD), complementary metal oxide semiconductor (CMOS)). The reporter molecule absorbance/luminescence from each SSTT-MIP-based sensor element is then related to the corresponding target analyte concentration in the sample.

The absorbance/luminescence from an SSTT-MIP sensor array can be detected with a wide variety of photonic detectors. Examples of photonic detectors include a photodiode, photomultiplier tube, charge coupled device (CCD) or CMOS based image detector. When the detection device is an array detector, an entire SSTT-MIP array of sensor elements can be evaluated simultaneously.

In another embodiment, pin printing methodologies can be used to develop sensor arrays for simultaneous multi-analyte detection. This allows a high-speed imprinting of a plurality of sensor elements on a substrate that can be excited by an extrinsic light source (laser, lamp) or on the face of a LED for direct, integrated excitation/sensing.

The invention is further described in the Examples presented below which are meant as illustrative and not intended to be restrictive in any way.

Example 1

This embodiment describes the preparation of a SSTT-MIP for the selective detection of DDT as the target analyte (FIG. 1). First, a sacrificial spacer molecule template (SSMT) was synthesized. For this example, this was a two-step process. In step 1, 4,4',4"-trihydroxytriphenylmethanol (HBHE) was prepared by using the synthetic strategy reported by Cushman

[31]. In step two, the complete SSMT was formed by reacting 1 eq of 4,4',4"-trihydroxytriphenylmethanol with an excess of 3-isocyanatopropyltriethyoxysilane (IPTES) in dry THF as described to form the tetracarbamate, (Compound 1) the SSMT. $^1$H and $^{13}$C NMR (500 MHz), IR, and MS data (not shown) were all consistent with the formation of all four carbamate bonds in Compound 1. The templated xerogel was then prepared by reacting 1 eq of Compound 1 with 100-500 eq of one of several alkoxides (see FIG. 1). This mixture was agitated for several minutes to several hours. After allowing the sol to hydrolyze in a sealed vial, thin films (500-800 nm, determined by profilometry) were spun cast onto a fused silica substrate and the xerogel was allowed to form in the dark, for 24-48 hours, at room temperature. The SSMT was removed from the templated xerogel by using 50-200 mM LiAlH$_4$ [17e] followed by a sequential rinse with THF, 0.1 M HCl, and 0.1 M NH$_3$. To install the reporter molecule into the templated site we contacted the templated xerogel films with 10-200 ppm DDT in THF to fill accessible templated sites with DDT. This left a single free amine residue (FIG. 1) within each template site. The reporter molecule was then introduced into the THF solution with a micropipette and the reaction between the free amine and the binding group in the reporter (—SO$_2$Cl) was allowed to proceed in the dark at room temperature for 2 hours. The xerogel film was then rinsed with fresh THF to remove any unreacted reporter molecule and DDT to create the SSTT-MIP.

Example 2

This example describes the use of SSMT-MIPs prepared as described in Example 1. FIG. 3 summarizes the response profiles from a series of xerogel-based SSTT-MIP films that were designed for the detection of DDT. The detector for these particular experiments was a photomultiplier tube. For these particular SSTT-MIPs, biphenyl was used as the R' residue (see FIG. 1). When DDT was added to the SSTT-MIP the fluorescence decreased (quenching) in step with the addition of DDT. As an initial test of the SSTT-MIP's selectivity for DDT these SSTT-MIP films in THF were reacted with an excess of phenyl-SO$_2$Cl to form a sulfonamide with any free amines. The response of the phenyl-SO$_2$Cl treated SSTT-MIP films was then re-determined. There was no observable response over the DDT concentration range tested. This result suggests that the phenyl-SO$_2$Cl accessed the templated sites in the SSTT-MIP in the absence of DDT and formed the sulfonamide with one or more of the free amine residues within the accessible DDT template site within the SSTT-MIP. In a second test, HBHE was introduced to SSTT-MIPs that were templated for DDT. HBHE, a hydroxylated DDT analog, was readily recognized by the SSTT-MIP; however, the observed response profile was completely different in comparison to DDT response. This result demonstrates that analyte-dependent response profiles are possible with the SSTT-MIPs. Again, when these SSTT-MIP films were treated with phenyl-SO$_2$Cl, there was no response to HBHE (results not shown). However, when a SSTT-MIP that was templated for DDT was initially challenged with a THF solution that contained 80 ppb HBHE, followed by the addition of 250 ppb DDT (waiting 15 min), the luminescence initially increased by 125±3% in the presence of HBHE and then decreased by 9±2% when the DDT was added. This result suggests that the DDT is able to displace some of the HBHE. Similarly, when a SSTT-MIP that was templated for DDT was challenged 60 ppb DDT, followed by the addition of 85 ppb HBHE, the luminescence dropped in the presence of DDT and then increased by 122±4% once the HBHE was added. This result suggests that the HBHE is able to displace some of the DDT. Together, these results indicate that SSTT-MIP strategy can be used for producing luminescence-based sensors that are analyte selective.

Example 3

This example elucidates some of the SSTT-MIP operational principles. The steady-state luminescence anisotropy (r) and multifrequency phase-modulation traces (equivalent to the time-resolved luminescence intensity decay) of the SSTT-MIP films (immersed in THF) with and without DDT or HBHE were recorded. The results are summarized in Table 2.

TABLE 2

Recovered steady-state luminescence anisotropies (r) and excited-state luminescence lifetimes for a DDT responsive SSTT-MIP.

| Sample | ΔF (%)[a] | r | τ (ns)/w (ns)[b] |
|---|---|---|---|
| SSTT-MIP | 0 | 0.10 ± 0.01 | 2.6 ± 0.06/1.2 ± 0.2 |
| SSTT-MIP + DDT | −27 | 0.36 ± 0.01 | 2.6 ± 0.1/0.1 ± 0.1 |
| SSTT-MIP + HBHE | +120 | 0.35 ± 0.01 | 3.4 ± 0.03/0.1 ± 0.1 |

[a]From FIG. 1 (100 ppb analyte).
[b]The excited-state luminescence lifetimes are reported in terms of a unimodal Lorentzian lifetime distribution where τ is the mean excited-state lifetime and w is the full width at half maximum for the distribution.

The Table reveals several important features. First, the Lissamine™ rhodamine B (LRB) residue's luminescence anisotropy is much smaller for the SSTT-MIP without analyte in comparison to the SSTT-MIP with analyte. Second, the intensity decay kinetics for the SSTT-MIP without analyte is clearly distributed, suggesting the luminophore (i.e., LRB) is encountering a distribution of microenvironments/cybotactic regions within the SSTT-MIP template site in the absence of analyte. Third, when DDT is added to the SSTT-MIP the mean LRB lifetime does not change. Fourth, when HBHE is added to the SSTT-MIP the mean LRB lifetime increases. Finally, the presence of analyte in the SSTT-MIP causes the lifetime to become single exponential. Together these results indicate the following: The luminescent report group within the SSTT-MIP template site without analyte is relatively mobile and it encounters a broad distribution of microenvironments/cybotactic regions. In the presence of DDT, the DDT molecules impede the luminophore's motion within the templated site, DDT forces the luminophore into a more discrete microenvironment or limits access to the other microenvironments, and the DDT quenches the luminophore fluorescence in a static manner (mean lifetime does not appear to change). In the presence of HBHE, the HBHE molecules impede the luminophore motion, HBHE forces the luminophore into a more discrete microenvironment, and the HBHE protects the luminophore from quenchers and/or increases the local microenvironment rigidity which causes an increase in the mean lifetime.

The FIG. 3 inset shows the response profile of a SSTT-MIP sensor film that was templated for DDT to repeated challenges by 150 ppb DDT. These continuous flow experiments were performed in a flowing THF stream by injecting 150 ppb plugs of DDT. The response time (time to reach 90% of the maximum signal change) for these 550±150 nm thick SSTT-MIP films is on the order of 20 s and the response is reversible to within 4% (20 cycles).

In FIG. 4 we summarize a series of response experiments for three different SSTT-MIP sensor films that were each templated for DDT. The only difference between these three SSTT-MIP films was the choice of the precursor ((EtO)$_3$—Si—(CH$_2$)$_2$—Si—(OEt)$_3$, (EtO)$_3$—Si-phenyl-Si—(OEt)$_3$, or (EtO)$_3$—Si-biphenyl-Si—(OEt)$_3$) that we used to form the final xerogel. Inspection of these data show several interesting features. First, these SSTT-MIP sensors are selective for DDT over a number of structurally similar analytes. Second, the R' group choice (FIG. 1) can be used to tune the overall sensor selectivity. Specifically, as the size of R' decreases, the overall DDT selectivity improves. These results demonstrate a strategy for forming arrays of SSTT-MIP-based sensor elements wherein each sensor element can be designed for a given analyte, and the collective response of the sensor elements for said analyte tailored. In this way multiple sensors can be designed for the detection of the same analyte; a redundant strategy that is self checking.

Example 4

This embodiment describes the SSMT-MIPs for the detection of two other analytes, namely codeine and digitoxin (morphine and digoxin, respectively, served to form the SSMTs). Table 3 shows the effect of variables such as xerogel composition, connecting moiety length and luminophore identity for a pair of SSTT-MIP-based sensors designed for the detection of codeine and digitoxin.

TABLE 3

Effects of xerogel composition, reporter, tether chemistry and length on analyte detection limits.

| Analyte | Xerogel[a] | Reporter | Pair[b] | Connecting Moiety[c] | Detection Limits |
|---|---|---|---|---|---|
| Codeine | d | Dansyl | NH$_2$/SO$_2$Cl | D | 25 nM |
|  | d | Dansyl | NH$_2$/SO$_2$Cl | C$_3$ | 90 nM |
|  | d | Dansyl | NH$_2$/SO$_2$Cl | C$_6$ | 700 nM |
|  | d | NBD | NH$_2$/SO$_2$Cl | D | 1.2 M |
|  | e | NBD | NH$_2$/SO$_2$Cl | D | 1.2 nM |
| Digitoxin | d | Dansyl | NH$_2$/SO$_2$Cl | D | 100 M |
|  | f | Dansyl | NH$_2$/SO$_2$Cl | D | 1.7 nM |
|  | g | Dansyl | NH$_2$/SO$_2$Cl | D | 1.9 nM |
|  | h | NBD | NH$_2$/SO$_2$Cl | D | 78 nM |

[a]Molar composition of the xerogel.
[b]Function group within the template site/functional bonding group.
[c]D - direct attachment of the bonding group to the luminophore, C$_3$ - propyl spacer between the bonding group and luminophore, C$_6$ - hexyl spacer between the bonding group and luminophore.
d) 45 mol % tetraethylorthosilane (TEOS), 5 mol % octyltrimethoxysilane (OTS), and 50 mol % bis (2-hydroxy-ethyl) aminopropyltriethoxysilane (HAPTS).
e) 85 mol % TEOS, 5 mol % OTS, and 10 mol % HAPTS.
f) 47 mol % TEOS, 33 mol % 3,3,3-trifluorpropyltrimethoxysilane (TFP-TMOS), and 20 mole % OTS.
g) 25 mole % TEOS, 40 mol % (pentafluorophenyl)-propyltrimethoxysilane (PFP-TMOS), and 35 mole % TFP-TMOS.
h) 50 mole % TEOS, 10 mol % PFP-TMOS, 10 mole % TFP-TMOS, 20 mole % OTS, and 10 mole % TFP-TMOS.

While specific embodiments have been presented in this description, those skilled in the art will recognize that routine modifications can be made by those skilled in the art without departing from the scope of the invention.

REFERENCES

1. *Commercial Biosensors. Applications to Clinical, Bioprocess, and Environmental Samples*; Ramsay, G., Ed.; John Wiley & Sons: New York, N.Y., 1998
2. Harris, T. D., "Think carefully, and take more data," *Anal. Chem.* 2000, 72, 669A.
3. Gopel, W., "From electronic to bioelectronic olfaction, or: From artificial "moses" to real noses," *Sens. Actuators B* 2000, B65, 70-72.
4. Albert, K. J.; Lewis, N. S.; Schauer, C. L.; Sotzing, G. A.; Stitzel, S. E.; Vaid, T. P.; Walt, D. R., "Cross-reactive chemical sensor arrays," *Chem. Rev.* 2000, 100, 2595-626.
5. Britton, C. L.; Jones, R. L.; Oden, P. I.; Hu, Z.; Warmack, R. J.; Smith, S. F.; Bryan, W. L.; Rochelle, J. M., "Multiple-input microcantilever sensors," *Ultramicroscopy* 2000, 82, 17-21.
6. Bailey, R. A.; Persaud, K. C. In *Polymer Sensors and Actuators*; Osada, Y.; DeRossi, D. E., Eds.: Springer-Verlag, Berlin, Germany, 2000; pp. 149-81.
7. Stefan, R.-I.; Van Staden, J. F.; Aboul-Enein, H. Y., "Electrochemical sensor arrays," *Crit. Rev. Anal. Chem.* 1999, 29, 133-53.
8. (a) Walt, D. R., "Imaging optical sensor arrays," Cur. Opin. Chein. Biol. 2002, 6, 689-95. (b) Liebsch, G.; Klimant, I.; Frank, B.; Holst, G.; Wolfbeis, O. S., "Luminescence lifetime imaging of oxygen, pH, and carbon dioxide distribution using optical sensors," *Appl. Spectrosc.* 2000, 54, 548-59. (c) Rakow, N. A.; Suslick, K. S., "A colorimetric sensor array for odor visualization," *Nature* 2000, 406, 710-3. (d) Liu, Y.-H.; Dam, T. H.; Pantano, P., "A pH-sensitive nanotip array imaging sensor," *Anal. Chim. Acta* 2000, 419, 215-25. (e) Rowe, C. A.; Tender, L. M.; Feldstein, M. J.; Golden, J. P.; Scruggs, S. B.; MacCraith, B. D.; Cras, J. J.; Ligler, F. S., "Array biosensor for simultaneous identification of bacterial, viral, and protein analytes," *Anal. Chem.* 1999, 71, 3846-52. (f) Walt, D. R., "Fiber optic imaging sensors," *Acc. Chem. Res.* 1998, 31, 267-78.
9. (a) Barko, G.; Abonyi, J.; Hlavay, J., "Application of fuzzy clustering and piezoelectric chemical sensor array for investigation on organic compounds," *Anal. Chim. Acta* 1999, 398, 219-26. (b) Wachter, E. A.; Thundat, T., "Micromechanical sensors for chemical and physical measurements," *Rev. Sci. Instrum.* 1995, 66, 3662-7.
10. (a) Grate, J. W., "Acoustic wave microsensor arrays for vapor sensing," *Chem. Rev.* 2000, 100, 2627-47. (b) Park, J.; Groves, W. A.; Zellers, E. T., "Vapor recognition with small arrays of polymer-coated microsensors. A comprehensive analysis," *Anal. Chem.* 1999, 71, 3877-86. (c) Ricco, A. J.; Crooks, R. M.; Osbourn, G. C., "Surface acoustic wave chemical sensor arrays: New chemically sensitive interfaces combined with novel cluster analysis to detect volatile organic compounds and mixtures," *Acc. Chem. Res.* 1998, 31, 289-96.
11. *Methods in Enzymology*, Mosbach, K., Ed., Vol. 135 and 136, Academic Press: Orlando, Fla., 1987.
12. *Protein Immobilization: Fundamentals and Applications*, Taylor, R. F., Marcel Dekker, Inc.: New York, N.Y., 1991; Chapter 8.
13. Weetall, H. H. *Immobilized Enzymes, Antigens, Antibodies, and Peptides: Preparation and Characterization*, Marcel Dekker, Inc.: New York, N.Y., 1975; Chapters 6 and 8.
14. (a) Cho, E. J; Tao, Z., Tehan, E. C; Bright, F. V., "Pin-printed biosensor arrays for simultaneous detection of glucose and 0$_2$," *Anal. Chem.* 2002 74, 6177-84. (b) Cho, E. J.; Bright, F. V., "Integrated chemical sensor array platform based on a light emitting diode, xerogel derived sensor elements, and high-speed pin printing," *Anal. Chim. Acta* 2002 470, 10 1-10. (c) Cho, E. J.; Bright, F. V., "Pin-printed chemical sensor arrays for simultaneous multi-analyte quantification," *Anal. Chem.* 2002 74, 1462-6. (d) Cho, E. J.; Bright, F. V., "Optical sensor array and integrated light source (OSAILS)," *Anal. Chem.* 2001, 73, 3289-93.
15. (a) Piletsky, S. A.; Alcock, S.; Turner, A. P. F., "Molecular imprinting: At the edge of the third millennium," *TrBC* 2001, 19, 9-12. (b) Katz, A.; Davis, M. E., "Molecular imprinting of bulk, microporous silica," *Nature* 2000, 403, 286-9. (c) Dickert, F. L.; Hayden, 0., "Molecular imprinting in chemical sensing," *TrAC* 1999, 18, 192-9. (d) Kriz, D.; Ramstrom, 0.; Mosbach, K., "Molecular imprinting. New possibilities for sensor technology," *Anal. Chem.* 1997, 69, 345A-9A. (e) Ensing, K.; De Boer, T., "Tailor-made materials for tailor-made applications: Application of molecular imprints in chemical analysis," *TrAC* 1999, 18, 138-45. (F) Wulff, G., "Molecular imprinting in crosslinked materials with the aid of molecular templates—A way towards artificial antibodies," *Ang. Chem., Int. Ed. Engl.* 1995, 34, 1812-32. (g) Mayes, A. G.; Mosbach, K., "Molecularly imprinted polymers: Useful materials for analytical chemistry?," *TrAC* 1997, 16, 321-32. (h) Mosbach, K., "Molecular imprinting," *TrBS* 1994, 19, 9-14. (i) Mallik, S.; Plunkett, S. D.; Dhal, P. K.; Johnson, R. D.; Pack, D.; Shnek, D.; Arnold, F. H., "Towards materials for the specific recognition and separation of proteins," *New. J. Chem.* 1994, 18, 299-304.

16. Leung, M. K.-P; Chow, C.-F.; Lam, M. H.-W., "A sol-gel derived molecular imprinted luminescent PET sensing material for 2,4-dichlorophenoxyacetic acid," *J. Mater. Chem.* 2001, 11, 2985-91.

17. Examples of fluorescence-based sensors that incorporate the fluorophore within the MIP include: (a) Turkewitsch, P.; Wandelt, B.; Darling, G. D.; Powell, W. S., "Fluorescent functional recognition sites through molecular imprinting. A polymer-based fluorescent chemosensor for aqueous cAMP," *Anal. Chem.* 1998, 70, 2025-30. (b) Jenkins, A L., Uy, O. M.; Murray, G. M., "Polymer-based lanthanide luminescent sensor for detection of the hydrolysis product of the nerve agent Soman in water," *Anal. Chem.* 1999, 71, 373-8. (c) Matsui, I.; Higashi, M.; Takeuchi, T., "Molecularly imprinted polymer as 9-ethyladenine receptor having a porphyrin-based recognition center," *J. Am. Chem. Soc.* 2000, 122, 5218-9. (d) Liao, Y.; Wang, W.; Wang, B., "Building fluorescent sensors by template polymerization: The preparation of a fluorescent sensor for L-tryptophan," *Bioorg. Chem.* 1999, 27, 463-76. (e) Graham, A. L.; Carison, C. A.; Edmiston, P. L., "Development and characterization of molecularly imprinted sol-gel materials for the selective detection of DDT," *Anal. Chem.* 2002, 74, 458-67.

18. (a) Whitcombe, M. J.; Rodriguez, M. E.; Villar, P.; Vulfson, E. N., "A new method for the introduction of recognition site functionality into polymers prepared by molecular imprinting: Synthesis and characterization of polymeric receptors for cholesterol," *J. Am. Chem. Soc.* 1995, 117, 7105-11. (b) Sellergren, B., "Noncovalent molecular imprinting: Antibody-like molecular recognition in polymeric network materials," *TrAC* 1997, 16, 310-20. (c) Whitcombe, M. J.; Vulfson, E. N., "Covalent imprinting using sacrificial spacers," *Tech. Instrumn. Anal. Chem.* 2001, 23, 203-12 and references cited therein.

19. *Chemical Processing of Advanced Materials*; Hench, L. L.; West J. K., Eds.; Wiley: New York, N.Y., 1992.

20. (a) Hench, L. L.; West, J. K., "The sol-gel process," *Chem. Rev.* 1990, 90, 53-72. (b) Sanchez, C.; Ribot, F., "Design of hybrid organic-inorganic materials synthesized via sol-gel chemistry," *New J. Chem.* 1994, 18, 1007-47.

21. Paul, A. *Chemistry of Glasses,* 2nd ed.; Chapman and Hall: New York, N.Y., 1990, pp. 51-85.

22. Brinker, C. J.; Scherer, G. W. *Sol-Gel Science*; Academic Press: New York, N.Y., 1989.

23. Avnir, D.; Braun, S.; Ottolenghi, M., "Encapsulation of organic molecules and enzymes in sol-gel glasses," in *Supramolecular Architecture. Synthetic Control in Thin Films and Solids*, Bein, T. Ed., ACS Symp. Ser., Vol. 499: Washington, D.C., 1992.

24. (a) Avnir, D.; Braun, S.; Lev, O.; Ottolenghi, M., "Enzymes and other proteins entrapped in sol-gel materials," *Chem. Mater.* 1994, 6, 160514. (b) Avnir, D., "Organic chemistry within ceramic matrices: Doped sol-gel materials," *Acc. Chem. Res.* 1995, 28, 328-34. (c) Blum, J.; Avnir, D.; Schumann, H., "Sol-gel encapsulated transition-metal catalysts, *CHEMTECH* 1999, 29, 32-8.

25. Avnir, D.; Braun, S.; Lev, O.; Levy, D.; Ottolenghi, M., "Organically doped sol-gel porous glasses: Chemical sensors, enzymatic sensors, electrooptical materials, luminescent materials and photonic materials," in *Sol-Gel Optics—Processing and Applications*, Klein, L. C., Ed., Kluwer: Boston, 1994, Chapter 23.

26. (a) Dave, B. C.; Dunn, B.; Valentine, J. S.; Zink, J. 1, "Sol-gel encapsulation methods for biosensors," *Anal. Chem.* 1994, 66, 1120A-7A. (b) Lan, E. H.; Dave, B. C.; Fukuto, J. M.; Dunn, B.; Zink, J. I.; Valentine, J. S., "Synthesis of sol-gel encapsulated heme proteins with chemical sensing properties," *J. Mater. Chem.* 1999, 9, 45-53.

27. Lev, O.; Tsionsky, M.; Rabinovich, L.; Glezer, V.; Sampath, S.; Pankratov, I; Gun, J., "Organically modified sol-gel sensors," *Anal. Chem.* 1995, 67, 22A-30A.

28. (a) Brennan, J. D., "Using intrinsic fluorescence to investigate proteins entrapped in sol-gel derived materials," *Appl. Spectrosc.* 1999, 53, 106A-21A. (b) Jin, W.; Brennan, J. D., "Properties and applications of proteins encapsulated within sol-gel derived materials," *Anal. Chem. Acta* 2002, 461, 1-36.

29. *Protecting Groups*, Kocienski, P., Thieme Publishers: New York, N.Y., 1994.

30. (a) Leonard, N. J.; Scott, T. G.; Huang, P., "Spectroscopic models related to coenzymes and base pairs. The basis for hypochromism in the ultraviolet spectra of model systems related to nicotinamide-adenine dinucleotide," *J. Am. Chem. Soc.* 1967, 89, 7137-8. (b) Browne, D. T.; Eisinger, J.; Leonard, N. J., "Synthetic spectroscopic models related to coenzymes and base pairs. II. Evidence for intramolecular base-base interactions in dinucleotide analogs," *J. Am. Chem. Soc.* 1968, 90, 7302-23.

31. Cushman, M.; Kanamathareddy, S.; De Clercq, E.; Schols, D.; Goldman, M. E.; Bowen, J. A., "Synthesis and anti-HIV activities of low molecular weight aurintricarboxylic acid fragments and related compounds," *J. Med. Chem.* 1991, 34, 337-42.

I claim:

1. A method of preparing a site selectively tagged molecularly imprinted polymer for specifically detecting a target analyte molecule comprising the steps of:
    a) combining unpolymerized polymer components with one or more sacrificial spacer molecular template (SSMT) molecules, wherein each SSMT molecule has at least one more reactive group than is needed for target analyte recognition;
    b) allowing polymerization of the unpolymerized components thereby forming templated sites in the polymer, wherein each templated site is bonded to the SSMT molecule via a plurality of bonds;
    c) releasing the SSMT molecules from the templated sites thereby forming templated sites having a plurality of exposed reactive groups such that the number of the exposed reactive groups at each templated site is at least one more than is needed for target analyte recognition;
    d) effecting non-covalent binding of the target analyte molecule to the templated site having the plurality of exposed reactive groups, wherein at least one exposed reactive group at each templated site is left free;

e) effecting covalent binding of a reporter molecule to the free at least one more exposed reactive group from d), wherein the reporter molecules in the polymer are exclusively present at the templated sites; and f) releasing the target analyte molecule thereby providing a site selectively tagged molecularly imprinted polymer, which can specifically detect the presence of the target analyte in a test sample.

2. The method of claim 1, wherein the polymer is a xerogel or an aerogel.

3. The method as in claim 1, wherein the at least one more reactive groups on the SSMT molecule comprises a hydroxyl group.

4. The method as in claim 1 wherein said reporter comprises a luminophore or a chromophore, a connecting group and a binding group.

5. The method of claim 1, wherein the reporter is a luminophore selected from the group consisting of dansyl, fluorescein, BODIPY, rhodamine, tris(4,7-diphenyl-1,10-phenanthroline)ruthenium(II) ([Ru(dpp)$_3$]$^{2+}$) and quantum dots.

6. The method of claim 1, wherein the reporter is a chromophore is selected from the group consisting of 4-nitroaniline; 2,6-diphenyl-4-(2,4,6-triphenyl-1-pyridinio)phenolate (Reichardt's dye 30); 2,6-dichloro-4-(2,4,6-triphenyl-1-pyridinio)phenolate; and N,N-diethyl-4-nitroaniline.

7. The method of claim 4, wherein the connecting group is selected from the group consisting of a methylene chain, ether chain, polydimethylsiloxane chain, polystyrene chain and amino acid chain.

8. The method of claim 4, wherein the binding group is selected from the group consisting of isothiocyanates, succinimidyl esters, carboxylic esters, tetrafluorophenyl esters, carbonyl azides, sulfonyl chlorides, arylating agents, aldehydes, iodoacetamides, maleimides, disulfides, dichlorotriazines, N-methylisatoic anhydride, aminophenylboronic acids, isocyanates prepared from acyl azides, acyl nitriles, hydrazines, hydroxylamines amines, carbodiimides, esterification reagents, diazoalkanes, alkyl halides and trifluoromethanesulfonates.

9. The method of claim 1, wherein the analyte is a compound selected from the group comprised of pharmaceuticals, prostaglandins, steroids, glycosides, deoxyribonucleosides and deoxyribonucleotides.

10. The method of claim 9, wherein the pharmaceuticals are selected from the group consisting of pheytoin, codeine, heroin, cocaine, Δ9-THC, tetracycline, morphine and the SSMT is respectively selected from the group consisting of 5-(p-hydroxyphenyl)-5-phenylhydantoin, morphine, 3-acetylmorphine, p-hydroxycocaine, 8-α-hydroxy-Δ9-THC, oxytetracycline and nalbuphine.

11. The method of claim 1, wherein the prostaglandins are selected from the group consisting of prostaglandin A2, prostaglandin B2, prostaglandin E1, prostaglandin E2, prostaglandin F1a, prostaglandin F2a, prostaglandin F2a, and the SSMT is respectively selected from the group consisting of 19(R)-hydroxyprostaglandin A2, 19(R)-hydroxyprostaglandin B2, 19(R)-hydroxyprostaglandin E1, 19(R)-hydroxyprostaglandin E2, 19(R)-hydroxyprostaglandin F1a, 19(R)-hydroxyprostaglandin F2a and 19(R)-hydroxyprostaglandin F2a.

12. The method of claim 1, wherein the steroids are selected from the group consisting of testosterone, estradiol, progesterone, cholesterol and the SSMT is respectively selected from the group consisting of 4-hydroxytestosterone, 4-hydroxyestradiol, 17-α-hydroxyprogesterone and 22(r)-hydroxycholesterol.

13. The method of claim 1, wherein the glycosides are selected from the group consisting of methyl α-D-glucopyrnoside, methyl β-D-glucopyrnoside, digitoxin, 2-deoxyribose and the SSMT is respectively selected from the group consisting of α-D-glucopyranose, β-D-glucopyranose, digoxin and ribose.

* * * * *